United States Patent
Furuzono et al.

(10) Patent No.: US 7,611,782 B2
(45) Date of Patent: Nov. 3, 2009

(54) TITANIUM OXIDE COMPLEX AND PRODUCTION METHOD THEREOF, AND MEDICAL MATERIAL USING THE SAME

(75) Inventors: Tsutomu Furuzono, Suita (JP); Akio Kishida, Toyonaka (JP)

(73) Assignee: Japan as Represented by the President of National Cardiovascular Center, Osaka (JP)

( * ) Notice: Subject to any disclaimer, the term of this patent is extended or adjusted under 35 U.S.C. 154(b) by 112 days.

(21) Appl. No.: 10/510,132

(22) PCT Filed: Dec. 12, 2003

(86) PCT No.: PCT/JP03/16003

§ 371 (c)(1),
(2), (4) Date: Oct. 4, 2004

(87) PCT Pub. No.: WO2005/019317

PCT Pub. Date: Mar. 3, 2005

(65) Prior Publication Data

US 2005/0228111 A1    Oct. 13, 2005

(30) Foreign Application Priority Data

Aug. 26, 2003    (JP)    ............................. 2003-208902

(51) Int. Cl.
*B32B 9/00*    (2006.01)
(52) U.S. Cl. .................................................. 428/701
(58) Field of Classification Search ................ 428/701, 428/698; 528/34; 604/265; 607/36
See application file for complete search history.

(56) References Cited

U.S. PATENT DOCUMENTS

| | | | | |
|---|---|---|---|---|
| 3,021,834 A | * | 2/1962 | Sheldon | 600/144 |
| 3,547,688 A | * | 12/1970 | Gagliardi et al. | 442/123 |
| 6,048,910 A | * | 4/2000 | Furuya et al. | 522/86 |
| 6,126,915 A | | 10/2000 | Tunashima et al. | |
| 6,228,796 B1 | | 5/2001 | Arakawa et al. | |

(Continued)

FOREIGN PATENT DOCUMENTS

JP    402109570    *    4/1990

(Continued)

OTHER PUBLICATIONS

K.B. Lehmann et al. "Studien über die hygienischen Eigenschaften des Titandioxyds und des Titanwei β" (Chemiker-Zeitung, No. 82 pp. 793-794 (1927)).

(Continued)

*Primary Examiner*—Jennifer McNeil
*Assistant Examiner*—Daniel Miller
(74) *Attorney, Agent, or Firm*—Nixon & Vanderhye P.C.

(57) ABSTRACT

A reactive functional group is introduced into titanium oxide, and an active group which is capable of reacting with the reactive functional group is introduced into a polymer-based material, and the reactive functional group and the active group are reacted with each other, thereby producing a titanium oxide complex in which the polymer-based material and the titanium oxide chemically bond to each other. Further, a functional group of the polymer-based material and the titanium oxide are reacted with each other, thereby producing the titanium oxide complex without performing chemical pretreatment with respect to the titanium oxide.

15 Claims, 4 Drawing Sheets

U.S. PATENT DOCUMENTS

| | | | |
|---|---|---|---|
| 6,239,194 | B1 | 5/2001 | Standke et al. |
| 6,716,908 | B2 * | 4/2004 | Lomas et al. ............... 524/588 |
| 6,968,234 | B2 * | 11/2005 | Stokes .......................... 607/36 |
| 2003/0018103 | A1 * | 1/2003 | Bardman et al. ............ 523/204 |
| 2003/0178296 | A1 | 9/2003 | Kato et al. |
| 2004/0126406 | A1 | 7/2004 | Kokubo et al. |

FOREIGN PATENT DOCUMENTS

| | | | |
|---|---|---|---|
| JP | 4-18453 A | | 1/1992 |
| JP | 9-278928 A | | 10/1997 |
| JP | 11-343425 A | | 12/1999 |
| JP | 2000-280397 A | | 10/2000 |
| JP | 2001-141905 A | | 5/2001 |
| JP | 2002-206021 A | | 7/2002 |
| JP | 2002331028 A | * | 11/2002 |
| JP | 2003-181299 A | | 7/2003 |
| WO | WO 97/24289 A1 | | 7/1997 |
| WO | WO 02/34301 A1 | | 5/2002 |

OTHER PUBLICATIONS

K. Yoshida et al. "Effects of Filler Composition and Surface Treatment on the Characteristics of Opaque Resin Composites" (J. Biomed. Mater. Res. Appl. Biomater 58, pp. 525-530 (2001)).

R. Cai et al. "Induction of Cytotoxicity by Photoexcited $TiO_2$ Particles" (Cancer Research 52, pp. 2346-2348 (1992)).

M. Kiyono "Titanium Oxide-Properties and Applied Technology" (pp. 80-81, pp. 118 (1991)).

T. Furuzono et al. "Development of Amino-Modified Titanium Dioxide/Silicone Composite" (Polymer Preprints, Japan, vol. 52, No. 5 p. 1130 (2003)) ($52^{nd}$ Annual Convention of Society of Polymer Science, Japan, held at Nagoya Congress Center from May 23-30, 2003).

Furuzono et al. "Development of nano-scaled titanium dioxide-silicone composite expressing cell adhesiveness and photoreactivity" (Proceedings of the convention, p. 71 (2003) ($25^{th}$ Convention of Japanese Society for Biomaterial held at Osaka International Convention Center, from Dec. 16-17, 2003).

S. Yasuda et al. "Properties of Titanium dioxide/Silicone composite material having cell adhesiveness and antibacterial effect" (Polymer Preprints, Japan, vol. 53, No. 1 p. 1965 (2004) ($53^{rd}$ Annual Convention of Society of Polymer Science, Japan, held at International Conference Center Kobe, from May 25-27, 2003).

T. Furuzono et al. "Photoreactivity and cell adhesiveness of amino-group-modified titanium dioxide nano-particles on silicone substrate coated by covalent linkage" (Journal of Materials Science Letters 22, pp. 1737-1740, (2003)).

T. Furuzono et al. "Establishment of Biointerface Required in Regeneration Medicine" (Program & Abstracts for $13^{th}$ Annual Meeting of Japan Society for Blood Purification in Critical Care (2002)) ($13^{th}$ Annual Meeting of Japan Society for Blood Purification in Critical Care, held at Keio Plaza Hotel, Sep. 26-27, 2004).

Office Action mailed Sep. 18, 2007 by the Japanese Patent Office for Japanese Patent Application No. 2003-208902.

Translation of Notice of Reasons for Refusal of Japanese Patent Application No. 1003-208902.

* cited by examiner

TITANIUM OXIDE COMPLEX AND PRODUCTION METHOD THEREOF, AND MEDICAL MATERIAL USING THE SAME

This application is the US national phase of International Application PCT/JP2003/016003 filed 12 Dec. 2003 which designated the U.S. and claims benefit of JP 2003-208902 dated 26 Aug. 2003, the entire content of which is hereby incorporated by reference.

TECHNICAL FIELD

The present invention relates to (i) a titanium oxide complex, having biocompatibility and adhesiveness (adhesion property) with respect to an anatomy, which is preferable in medical use, (ii) a production method of the titanium oxide complex, and (iii) a medical material using the complex.

BACKGROUND ART

A polymer-based material such as silicone rubber and polyurethane has properties such as a bioinert property, long-term stability, strength, and flexibility, and is widely used as a medical material such as a percutaneous catheter for example. However, since the exemplified polymer-based material is bioinert, its percutaneous portion may not adhere to an anatomy, so that this embraces a possibility that: skin downgrowth (phenomenon in which an epithelial tissue is internally convoluted along a surface of a catheter) may occur, and there may be a risk of bacterial infection in the convoluted tissue.

Titanium oxide is mixed and combined with a coating material, synthesis resin, ink, paper, chemical fiber, and the like, by making use of its property as white pigment. Further, titanium oxide is used, as a photocatalyst, in a deodorant, an antifoulant, an anti-bacterial/antiviral/antifungal material, an anticlouding agent, a water-treatment agent, an anticancer agent (material), and the like. Further, the titanium oxide is known as a substance, having a chemically great stability, which is free from any toxicity. Specifically, for example, it was reported that: no toxic symptoms was observed in (i) an animal experiment (L. Herget, Chem. Ztg., 82,793 (1929)) in which animal feeding stuffs containing titanium oxide was given for 16 months and (ii) an animal experiment (L. Vernettiblinate, Riforma. Med. Naples, 44,15,16 (1928)) in which hypodermic injection of titanium oxide was performed and powder of titanium oxide was inhaled. Moreover, it was reported that: no carcinogen was observed even when oral administration of titanium oxide was performed (D. S. Fredrickson, Federal Register, 43,225,54299 (1978)).

As a medical material using the titanium oxide, there are proposed (i) a dental resin composite filler having a high covering power (K. Yoshida, et al., J. Biomed. Mater. Res. Appl. Biomater., 58,525 (2001)), (ii) an anticancer agent based on a photocatalysis (R. Cai, et al., Cancer Res., 52,2346 (1992)), and (iii) a catheter which does not adhere to liquid containing substance.

Further, there is proposed a titanium oxide complex, obtained by combining the titanium oxide with the aforementioned polymer-based material, which is favorable in medical use.

A specific example of the production method of the titanium oxide complex includes "blending" based on infiltration or melting. Further, examples of a method for coating a surface of the polymer-based material with titanium oxide include a dip method, a spin coat method, a spray method, a screen printing method, and the like.

However, in the titanium oxide complex produced by the foregoing production methods, essential properties of the polymer-based material and the titanium oxide are varied. Alternatively, there is a problem that the titanium oxide exfoliates from the polymer-based material.

Specifically, in case of the titanium oxide complex produced in accordance with infiltration or melting, the essential property of the titanium oxide or the polymer-based material is lost or varied in the production process.

Further, in the titanium oxide complex produced in accordance with the method of coating the surface of the polymer-based material with the titanium oxide, the merely application of the titanium oxide to the surface of the polymer-based material is performed, that is, the titanium oxide is made to physically adhere or stick to the surface of the polymer-based material. Thus, the titanium oxide is liable to exfoliate from the surface of the polymer-based material. When the titanium oxide is liable to exfoliate from the surface of the polymer-based material in this manner, it is impossible to exhibit a function as the titanium oxide complex.

Therefore, it is required to provide (i) a titanium oxide complex in which titanium oxide firmly bond to a surface of a polymer-based material in a simple manner without deteriorating essential properties of the titanium oxide and the polymer-based material and (ii) a production method of the titanium oxide complex.

DISCLOSURE OF INVENTION

In order to solve the foregoing problems, a titanium oxide complex of the present invention includes: a polymer-based material having an active group; and titanium oxide having a reactive functional group which is capable of reacting with the active group, wherein the active group and the reactive functional group are bonded to each other based on a chemical bond.

According to the arrangement, the titanium oxide and the polymer-based material chemically bond to each other. Thus, compared with a conventional titanium oxide complex, it is possible to firmly fix the titanium oxide and the polymer-based material to each other. Therefore, it is possible to fix (root) the titanium oxide to a surface of the polymer-based material for an extended period of time.

Further, according to the arrangement, a combination which enables the active group and the reactive functional group to enter into a chemical bond is selected, so that it is possible to chemically bond the polymer-based material and the titanium oxide to each other more easily.

In order to solve the foregoing problems, the titanium oxide complex of the present invention, obtained by chemically bonding titanium oxide to a polymer-based material having a functional group which is capable of chemically bonding to the titanium oxide, is arranged so that the titanium oxide and the functional group chemically bond directly to each other.

"The titanium oxide and the functional group, which is capable of reacting with the titanium oxide of the polymer-based material, chemically bond directly to each other" means that the titanium oxide and the functional group chemically bond directly to each other. That is, in the titanium oxide complex of the present invention, the polymer-based material and the titanium oxide itself chemically bond to each other.

Examples of a complexation method of the titanium oxide are as follows. (1) A method in which: after modifying a surface of the titanium oxide and/or the polymer-based material (surface treatment), both the titanium oxide and the polymer-based material are made to chemically bond to each other. (2) A method in which: the titanium oxide and the polymer-based material are made to chemically bond to each other without performing the surface treatment.

As to the method (1), it is not necessary to perform chemical pretreatment with respect to the titanium oxide in a process of performing the surface treatment with respect to merely the polymer-based material, that is, a process of chemically bonding (i) the titanium oxide which has not been subjected to any chemical surface treatment directly to (ii) the functional group which is capable of chemically bonding to the titanium oxide of the polymer-based material. Note that, the chemical surface treatment means to introduce the active group and the like into the titanium oxide.

Further, the titanium oxide itself and the functional group of the polymer-based material are made to chemically bond directly to each other, so that there is no possibility that the active group remaining on the surface of the titanium oxide may damage a characteristic (property) of the titanium oxide compared with the arrangement in which the active group is introduced into the titanium oxide.

In order to solve the foregoing problems, the medical material of the present invention includes the foregoing titanium oxide complex.

According to the arrangement, the medical material is arranged by using the foregoing titanium oxide complex. Thus, even in case of implanting the titanium oxide complex in a living body for an extended period of time, it is possible to provide a medical material having higher reliability.

In order to solve the foregoing problems, a method of the present invention for producing a titanium oxide complex, obtained by chemically bonding titanium oxide to a polymer-based material having a functional group which is capable of chemically bonding to the titanium oxide, includes: an active group introduction step of introducing an active group into the polymer-based material; a reactive functional group introduction step of introducing a reactive functional group, which is capable of reacting with the active group, into the titanium oxide; and a reaction step of reacting the active group with the reactive functional group.

According to the arrangement, the active group is introduced into the polymer-based material, and the reactive functional group is introduced into the titanium oxide, thereby chemically bonding the active group and the reactive functional group to each other. Thus, it is possible to easily produce the titanium oxide complex in which the titanium oxide and the polymer-based material chemically bond to each other.

In order to solve the foregoing problems, a method of the present invention for producing a titanium oxide complex, obtained by chemically bonding titanium oxide to a polymer-based material, includes an introduction step of introducing the functional group, which is capable of chemically bonding to the titanium oxide, into the polymer-based material; and a functional group reaction step of reacting the functional group of the polymer-based material with the titanium oxide.

According to the arrangement, the functional group which is capable of chemically bonding to the titanium oxide is introduced into the polymer-based material, so that it is not necessary to perform chemical pretreatment with respect to the titanium oxide. Thus, there is no possibility that the chemical pretreatment may damage or denature a property of the titanium oxide.

For a fuller understanding of the nature and advantages of the invention, reference should be made to the ensuing detailed description taken in conjunction with the accompanying drawings.

BEST MODE FOR CARRYING OUT THE INVENTION

Embodiment 1

Figure 1:
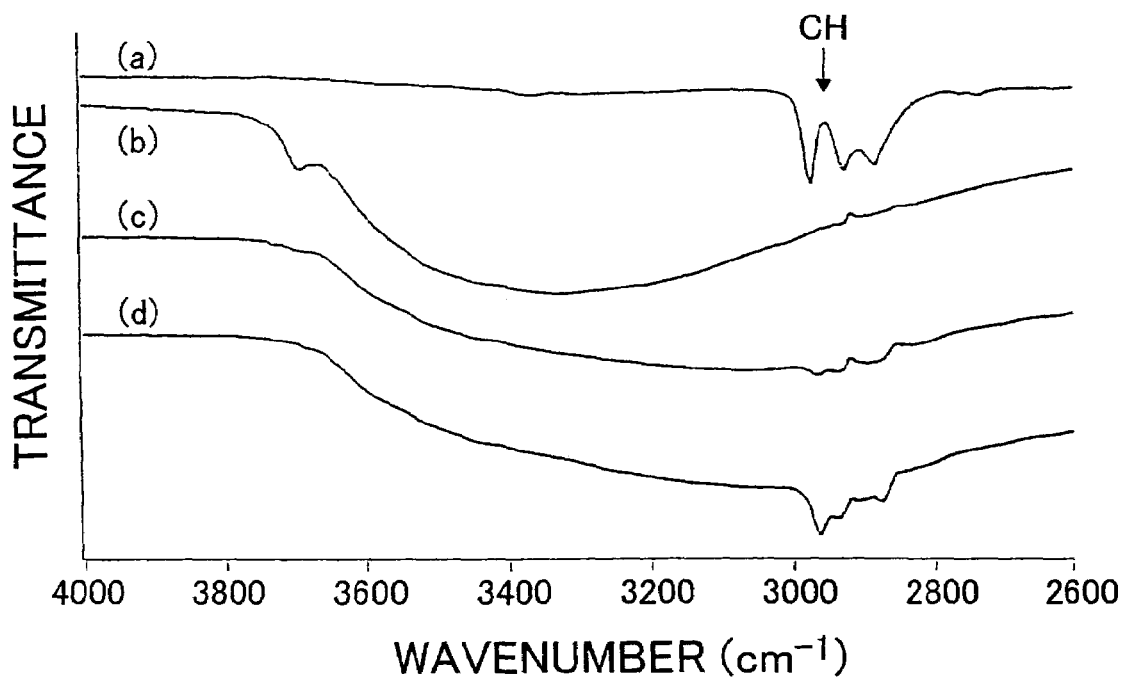
FIG. 1 shows infrared absorption spectra of γ-aminopropyltriethylsilane, titanium oxide, and aminated titanium oxide, that are described in Example.

One embodiment of the present invention is described below.

A titanium oxide complex according to the present embodiment is obtained by chemically bonding titanium oxide to a polymer-based material. In more detail, the titanium oxide complex includes: a polymer-based material having an active group; and titanium oxide having a reactive functional group which is capable of reacting with the active group, wherein the active group chemically bond to the reactive functional group.

(Titanium Oxide)

Titanium oxide according to the present embodiment is a compound represented by chemical formula such as $TiO_2$ and the like for example, and a surface thereof has a hydroxyl group. That is, the titanium oxide according to the present embodiment is titanium oxide having a hydroxyl group on a surface thereof.

Specifically, in case of $TiO_2$, there are two kinds of hydroxyl groups on crystal faces occupying a largest area in a surface of titanium oxide, i.e., an anatase-type (001) face and a rutile-type (110) face. The one of the crystal faces is a terminal OH group combined with $Ti^{4+}$, and the other is a bridge OH group combined with two $Ti^{4+}$s (*Property and Application of Titanium Oxide*, written by Manabu Kiyono, Published by Gihodo-syuppan, 2000).

Further, the titanium oxide according to the present embodiment is superior in (i) affinity with an anatomy and (ii) stability in a vital circumstance, so that the titanium oxide is favorably used as a medical material.

It is more preferable that the titanium oxide is particulate. In case where the titanium oxide is particulate, a shape and a diameter of titanium oxide particles are set so that a chemical bond between the titanium oxide and the polymer-based material described later enables the titanium oxide particles to be fixed on a surface of the polymer-based material. Specifically, a lower limit of the particle diameter is more preferably 0.001 μm or more, still more preferably 0.01 μm or more. Meanwhile, an upper limit of the particle diameter is more preferably 1000 μm or less, still more preferably 100 μm or less. When the particle diameter exceeds 1000 μm, or when the particle diameter is less than 0.001 μm, the bond between the titanium oxide and the polymer-based material described later is relatively weak. Thus, in case where the titanium oxide complex is implanted into a living organism, the titanium oxide complex may be damaged.

(Polymer-Based Material)

As the polymer-based material according to the present embodiment, it is more preferable to use a medical polymer material, and it is still more preferable to use organic polymer. Specific examples of the polymer-based material include: synthetic polymer such as silicone polymer (silicone rubber may be used), polyethyleneglycol, polyalkyleneglycol, polyglycolic acid, polylactic acid, polyamide, polyurethane, polysulfone, polyether, polyetherketone, polyamine, polyurea, polyimide, polyester, polyethylene, polypropylene, polytetrafluoroethylene, polyacrylic acid, polymethacrylic acid, polymethacrylatemethyl, polyacrylonitrile, polystyrene, polyvinylalcohol, and polyvinylchloride; and natural polymer such as (i) polysaccharide such as cellulose, amylose, amylopectin, chitin, and chitosan, and (ii) polypeptide such as collagen, (iii) mucopolysaccharide such as hyaluronic acid, chondroitin, and chondroitin sulfate, and (vi) silkfibroin, and the like. Out of the exemplified polymer-based materials, it is preferable to use silicone polymer, polyurethane, polytetrafluoroethylene, or silkfibroin, since they are superior in properties such as long-term stability, strength, and flexibility.

Instead of the polymer-based material mentioned above as an example, specifically, it is possible to use a base material constituted of inorganic material such as titanium alloy which can be favorably used as a medical material. Thus, the polymer-based material according to the present invention also includes the base material constituted of inorganic material such as titanium alloy.

Further, the polymer-based material may be in a sheet shape, a fiber shape, a tube shape, or a madreporite shape for example. Each of them is selected as required depending on use thereof.

(Production Method of Titanium Oxide Complex)

Here, a method according to the present embodiment for producing the titanium oxide complex is described as follows.

The method according to the present embodiment for producing the titanium oxide complex is roughly classified into two methods. That is, there are (1) a method in which the polymer-based material and the titanium oxide are made to chemically bond to each other after modifying surface(s) of the polymer-based material and/or the titanium oxide and (2) a method in which the polymer-based material and the titanium oxide are made to chemically bond to each other without performing surface treatment of both the polymer-based material and the titanium oxide.

The present embodiment will describe the foregoing method (1) for producing the titanium oxide complex, obtained by chemically bonding titanium oxide to a polymer-based material, includes: an active group introduction step of introducing an active group into the polymer-based material; a reactive functional group introduction step of introducing a reactive functional group, which is capable of reacting with the active group, into the titanium oxide; and a reaction step of reacting the active group with the reactive functional group.

More specifically, for example, silicone rubber obtained by performing graft polymerization with respect to a vinyl polymerization monomer having a carboxyl group on its surface is used as the polymer-based material having the active group, and titanium oxide obtained by introducing an amino group into its surface is used as titanium oxide particles obtained by introducing the reactive functional group into its surface, and they are reacted with each other, thereby producing the titanium oxide complex according to the present embodiment. This process is described below as an example.

That is, the active group and the reactive functional group are reacted with each other, thereby obtaining a chemical bond between the titanium oxide and the polymer-based material.

The chemical bond of the titanium oxide complex according to the present embodiment, that is, the chemical bond between the titanium oxide and the polymer-based material is not particularly limited as long as it is possible to obtain sufficient bonding strength between the titanium oxide and the polymer-based material. However, examples of the chemical bond are as follows.

Chemical Formula (1)

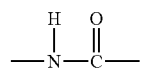

Chemical Formula (2)

(1)

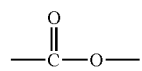

Chemical Formula (3)

(2)

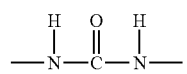

Chemical Formula (4)

(3)

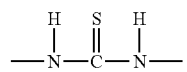

Chemical Formula (5)

(4)

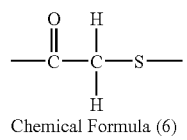

Chemical Formula (6)

(5)

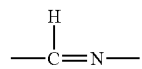

Chemical Formula (7)

(6)

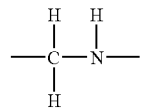

Chemical Formula (8)

(7)

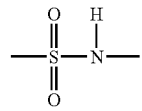

Chemical Formula (9)

(8)

-continued

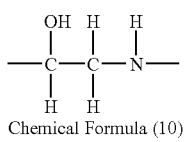
Chemical Formula (10)

(9)

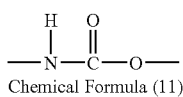
Chemical Formula (11)

(10)

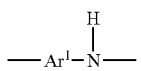

Chemical Formula (12)

(11)

—Ar²—S—

(12)

Chemical Formula (13)

—CH₂—CH₂—S—S—

(13)

Chemical Formula (14)

—S—

(14)

Chemical Formula (15)

Chemical Formula (16)

(15)

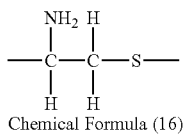

(16)

These chemical bonds can be obtained by reacting the reactive functional group introduced into the titanium oxide with the active group introduced into the polymer-based material.

The following description specifically explains an amido group, represented by chemical formula (1), out of the aforementioned chemical bonds. An amido bond can be obtained by causing reaction such as: reaction of an amino group with a carboxyl group, an azidocarbonyl group, a chlorocarbonyl group, an N-hydroxysuccinimide carboxylate ester, or acid anhydride; reaction of a carboxyl group with an N-acetylamino group or an N-trimethylsilyl amino group; reaction of an isocyanate group with a carboxyl group; and the like. An appropriate reaction condition varies depending on combinations thereof. As long as the reaction is proceeded, the reaction condition is not particularly limited.

For example, in case of a combination of the amino group and the carboxyl group, first, the titanium oxide is added to a solvent, and is stirred. After dispersing the titanium oxide, the polymer-based material is soaked therein. Further, the polymer-based material is picked up from the solvent. Thereafter, the polymer-based material is washed, and the active group of the polymer-based material and the reactive functional group of the titanium oxide are reacted with each other (condensation reaction) under a specific reaction condition.

At this time, a lower limit of an amount of the titanium oxide used is more preferably 0.001 weight part or more, still more preferably 0.01 weight part or more, with respect to 1 weight part of the polymer-based material having the active group. Meanwhile, an upper limit of the amount of the titanium oxide used is more preferably 100 weight parts or less, still more preferably 50 weight parts or less, with respect to 1 weight part of the polymer-based material having the active group. When the lower limit is less than 0.001 weight parts, titanium oxide particles are not evenly adsorbed to a surface of the polymer-based material, so that it may be impossible to form an even coating surface. Meanwhile, when the upper limit exceeds 100 weight parts, it is not economical.

Further, specific examples of the solvent in which the titanium oxide is dispersed include: water; a hydrocarbon solvent such as toluene and hexane; alcohols; an ether solvent such as tetrahydrofuran and diethyl ether; a ketone solvent such as acetone and methylethyl ketone; and the like. A lower limit of an amount of the solvent used is more preferably 0.1 weight part or more, still more preferably 1.0 weight part or more, with respect to 1 weight part of the polymer-based material. When the lower limit is less than 1 weight part, the titanium oxide particles are not evenly adsorbed to the surface of the polymer-based material, so that it may be impossible to form an even coating surface. Meanwhile, an upper limit of the amount of the solvent used is more preferably 1000 weight parts or less, still more preferably 500 weight parts or less, with respect to 1 weight part of the polymer-based material. When the upper limit exceeds 1000 weight parts, it is not economical.

Further, after the polymer-based material is picked up from the solvent, a lower limit of reaction temperature at which the active group of the polymer-based material reacts with the reactive functional group of the titanium oxide is set to be more preferably 120° C. or higher, still more preferably 140° C. or higher, particularly preferably 160° C. or higher. When the reaction temperature is lower than 120° C., the condensation reaction may be insufficiently proceeded. Meanwhile, an upper limit of the reaction temperature is more preferably 200° C. or lower, still more preferably 180° C. or lower. When the reaction temperature exceeds 200° C., the polymer-based material may be deteriorated.

Further, it is preferable to perform the condensation reaction under a reduced pressure. A lower limit of the reduced pressure is more preferably 0.01 mmHg (1.33 Pa) or more, still more preferably 0.1 mmHg or more. When the lower limit of the reduced pressure is lower than 0.01 mmHg, it is not economical in terms of equipments such as an apparatus. Meanwhile, an upper limit of the reduced pressure is more preferably 10 mmHg (1.33 kPa) or less, still more preferably 5.0 mmHg or less. When the upper limit of the reduced pressure is higher than 10 mmHg, it is difficult to cause the condensation reaction, so that it takes long time to perform the reaction. Further, in case of obtaining the amido bond between the amino group and the carboxyl group, it is possible to synthesize the amido bond at low temperature by using a condensing agent such as carbodiimide. Specifically, for example, it is possible to synthesize the amido bond by performing the reaction at temperature of 4° C. to room temperature (25° C.) for 1 to 6 hours.

Further, an ester bond represented by the chemical formula (2) can be obtained by reaction of the carboxyl group with the hydroxyl group, a diazo-carbonyl group and/or a diazo-alkyl group, or in a similar manner. An appropriate reaction condition varies depending on combinations thereof, and is not particularly limited. Specifically, in case of a combination of the carboxyl group and the hydroxyl group for example, it is possible to adopt a method, in which the carboxyl group and the hydroxyl group are reacted with each other in an organic solvent, or a similar method.

A urea bond represented by the chemical formula (3) can be obtained by reacting the amino group with the isocyanate group. A reaction condition is not particularly limited, but it is possible to adopt a method, in which the amino group and the isocyanate group are reacted with each other in the organic solvent at room temperature for example, or a similar method.

A thiourea bond represented by the chemical formula (4) can be obtained by reacting the amino group with the isocyanate group. A reaction condition is not particularly limited, but it is possible to adopt a method, in which the amino group and the isocyanate group are reacted with each other in a sodium carbonate buffer solution of pH9 within a temperature range of from 0° C. to room temperature for 1 to 24 hours for example, or a similar method.

A β-ketothioether bond represented by the chemical formula (5) can be obtained by reacting a mercapto group with an α-haloacetyl group, or in a similar manner. A reaction condition is not particularly limited, but it is possible to adopt a method, in which the mercapto group and the α-haloacetyl group are reacted with each other in water at room temperature under an alkalescent condition of pH7 to 8 for example, or a similar method.

A Schiff base structure represented by the chemical formula (6) can be obtained by reacting the amino group with a portion, which can function as aldehyde or ketone, or in a similar manner. As a reaction condition, it is possible to adopt a method, in which the amino group and the portion which can function as aldehyde or ketone are reacted with each other in an alkaline aqueous solution, or a similar method. Further, the Schiff base structure is reduced by using a known reducer such as sodium borohydride and cyano sodium borohydride, thereby obtaining a secondary and tertiary-amine structure represented by the chemical formula (7).

A sulfamide bond represented by the chemical formula (8) can be obtained by reacting the amino group with a chlorosulfonyl group or a sulfone group, or in a similar manner. An appropriate reaction condition varies depending on combinations thereof, and is not particularly limited. Specifically, in case of a combination of the amino group and the sulfonyl group, it is possible to adopt (i) a method in which the amino group and the sulfonyl group are reacted with each other in an organic solvent at room temperature and (ii) a method in which the amino group and the sulfonyl group are reacted with each other in water under an alkaline condition of pH9 to 10, or a similar method.

A hydroxy-secondary amine structure represented by the chemical formula (9) can be obtained by reacting the amino group with an epoxy group. A reaction condition is not particularly limited, but it is possible to adopt a method in which the amino group and the epoxy group are reacted with each other in water at room temperature under a condition of pH8 to 10, or a similar method.

A carbamate bond represented by the chemical formula (10) can be obtained by reacting the hydroxyl group with the isocyanate group or a diester carbonate, or in a similar manner. An appropriate reaction condition varies depending on combinations thereof, and is not particularly limited. For example, in case of a combination of the hydroxyl group and the isocyanate group, it is possible to adopt a method, in which the hydroxyl group and the isocyanate group are reacted with each other in a toluene solvent under reflux, or a similar method.

An arylamine structure represented by the chemical formula (11) can be obtained by reacting the amino group with an aryl halide group or a sulfonated aryl group, or in a similar manner. An appropriate reaction condition varies depending on combinations thereof, but is not particularly limited. Specifically, in case of the amino group and the aryl halide group for example, it is possible to adopt a method, in which the amino group and the aryl halide group are reacted with each other in aqueous solution under an alkaline condition, or a similar method. Note that, $Ar^1$ in the chemical formula (11) represents an aryl group.

An arylthioether represented by the chemical formula (12) can be obtained by reacting a mercapto group with the aryl halide group or the sulfonated aryl group, or in a similar manner. An appropriate reaction condition varies depending on combinations thereof, and is not particularly limited. Specifically, in case of the mercapto group and the aryl halide group, the mercapto group and the aryl halide group are reacted with each other in a methanol solvent by using piperidine as catalyst at 0° C. Note that, $Ar^2$ in the chemical formula (12) represents an aryl group.

A sulfide bond represented by the chemical formula (13) can be obtained by performing exchange reaction between the mercapto group and the sulfide bond. An appropriate reaction condition is not particularly limited. For example, it is possible to adopt a method, in which the mercapto group and the sulfide bond are reacted with each other in an aqueous solution of pH7 to 8 at room temperature, or a similar method.

A thioether bond represented by the chemical formula (14) can be obtained by reacting the mercapto group with an acryloyl group or imide maleate, or in a similar manner. An appropriate reaction condition varies depending on combinations thereof, and is not particularly limited. Specifically, in case of the mercapto group and the acryloyl group for example, it is possible to adopt a method, in which the mercapto group and the acryloyl group are reacted with each other in a neutral or alkaline solution, or a similar method.

A β-aminothioether bond represented by the chemical formula (15) can be obtained by reacting the mercapto group with aziridine or imine, or in a similar manner. An appropriate reaction condition varies depending on combinations thereof, and is not particularly limited. Specifically, in case of the mercapto group and an aziridine group for example, it is possible to adopt a method, in which the mercapto group and the aziridine group are reacted with each other in an aqueous solution under an alkalescent condition, or a similar method.

A vinyl bond represented by the chemical formula (16) can be obtained by performing vinyl polymerization reaction and the like. An appropriate reaction condition varies depending on combinations thereof, and is not particularly limited. Specifically, for example, it is possible to adopt a method, in which a vinyl group compound of the polymer-based material is subjected to graft polymerization so as to be combined with $TiO_2$ particles (titanium oxide particles) obtained by introducing a vinyl group, or a similar method.

These chemical bonds can be obtained by performing reaction between (i) the reactive functional group on a particle surface of the titanium oxide and (ii) the active group on a surface of the polymer-based material. Thus, in each of the aforementioned combinations, the one is the reactive functional group, and the other is the active group. Specifically, in case of obtaining the amido bond represented by the chemical formula (1) by reacting the amino group with the carboxyl group, the amino group may be the active group, or may be the reactive functional group. Likewise, the carboxyl group may be the reactive functional group, or may be the active group.

(Active Group Introduction Step)

Here, a step of introducing the active group into the polymer-based material (active group introduction step) is described.

Examples of a method for introducing the active group into the polymer-based material include: a method in which a surface graft polymerization is performed after performing, for example, an acid/alkaline treatment, corona discharge, and/or plasma irradiation with respect to a surface of the polymer-based material; and the like.

The following description explains an example of a method in which the active group is introduced by performing the surface graft polymerization treatment in case where polydimethylcyclohexane silicone rubber is used as the polymer-based material.

In the case of introducing the active group into the polydimethylcyclohexane silicone rubber, which is used as the polymer-based material, in accordance with the graft polymerization, first, the surface of the polymer-based material is subjected to the corona discharge or the plasma irradiation. Thereafter, thus treated polymer-based material and a polymerization monomer having the active group are placed in a solvent, and are polymerized in an inert gas atmosphere under a reduced pressure.

Examples of the solvent include: water; a hydrocarbon solvent such as toluene and hexane; alcohols; an ether solvent such as tetrahydrofuran and diethyl ether; a ketone solvent such as acetone and methylethylketone; and the like. A lower limit of an amount of the solvent used is more preferably 0.1 weight part or more, still more preferably 1.0 weight part or more, with respect to 1 weight part of the polymer-based material that has been treated. When the amount of the solvent used is less than 0.1 weight part, it is difficult to evenly introduce the active group into the surface of the polymer-based material. Meanwhile, an upper limit of the used solvent is more preferably 1000 weight parts or less, more preferably 500 weight parts or less, with respect to 1 weight part of the polymer-based material that has been treated. When the amount of the solvent used exceeds 1000 weight parts, it is not economical.

Further, the polymerization monomer used in the graft polymerization is not particularly limited as long as the polymerization monomer has the active group, which forms a chemical bond by reacting with the reactive functional group on a surface of the titanium oxide particles, in its end (side chain). In other words, the polymerization monomer has the active group for forming the chemical bonds represented by the chemical formula (1) to (16). Examples of the polymerization monomer include: (meth)acrylic acid, aconitic acid, itaconic acid, mesaconic acid, citraconic acid, fumaric acid, maleic acid, vinyl sulfonic acid, acrylamide-2-methylpropane sulfonic acid, vinyl sulfonic acid, and various metallic salts thereof or halides thereof; (meth)acrylamide, 2-hydroxyethyl(meth)acrylate, (meth)monoglycerol acrylate, N-[tris(hydroxymethyl)methyl]acrylamide, N-vinylpyrrolidone, N-(meth)acryloylpyrrolidone, acryloylmorpholine, imide maleate, maleic anhydride; a styrene monomer such as aminostyrene and carboxystyrene; glycidyl(meth)acrylate, (meth)acryloyloxyethyltrimethoxysilane, vinylbenzylamine, and the like.

A lower limit of an amount of the added polymerization monomer is more preferably 0.001 weight part or more, still more preferably 0.01 weight part or more, with respect to 1 weight part of the titanium oxide particles. When the amount of the added polymerization monomer is less than 0.001 weight part, it is difficult to introduce a sufficient amount of the active group into the surface of the polymer-based material. Meanwhile, an upper limit of the amount of the added polymerization monomer is more preferably 100 weight parts or less, still more preferably 50 weight parts or less, with respect to 1 part weight of the titanium oxide particles. When the amount of the added polymerization monomer exceeds 100 weight parts, it is not economical.

Further, a lower limit of polymerization temperature at which the polymer-based material and the polymerization monomer are polymerized with each other is more preferably 40° C. or higher, and still more preferably 50° C. or higher. When the polymerization temperature is lower than 40° C., the graft polymerization may be insufficiently performed. Meanwhile, an upper limit of the polymerization temperature is more preferably 100° C. or lower, and still more preferably 80° C. or lower. When the polymerization temperature exceeds 100° C., a graft efficiency may drop.

Further, in order to introduce, for example, a vinyl group into the polymer-based material as the active group, the polymer-based material and an active group containing compound are reacted with each other in a mixed solution of catalyst, polymerization inhibitor, and a solvent.

Specifically, examples of the active group containing compound include 2-methacryloyloxyethylisocyanate, hexamethylene diisocyanate, and the like. As the solvent, it is preferable to use a polar solvent. For example, anhydrous dimethyl sulfoxide, anhydrous dimethylformamide, and the like are favorably used. The polymerization inhibitor is added so that active groups introduced into the polymer-based material are not polymerized with each other and active group containing compounds are not polymerized with each other. Examples of the polymerization inhibitor include hydroquinone and the like. Examples of the catalyst include dibutyltin (IV) dilaurate, and the like.

A lower limit of an amount of the added active group containing compound is more preferably 10% by weight or more, more preferably 50% by weight, particularly preferably 100% by weight or more, with respect to the polymer-based material. When the amount of the added active group containing compound is less than 10% by weight, the active group may be insufficiently introduced. Meanwhile, an upper limit of the amount of the added active group containing compound is more preferably 500% by weight or less, still more preferably 400% by weight, particularly preferably 300% by weight or less, with respect to the polymer-based material. When the amount of the added active group containing compound exceeds 500% by weight, it is not economical.

Further, a lower limit of reaction temperature is more preferably 30° C. or higher, still more preferably 40° C. or higher, particularly preferably 45° C. or higher. When the reaction temperature is lower than 30° C., the reaction is not sufficiently brought about, so that there is a case where the active group is not introduced into the polymer-based material. Meanwhile, an upper limit of the reaction temperature is more preferably 100° C. or lower, still more preferably 80° C. or lower, particularly preferably 60° C. or lower. When the reaction temperature exceeds 100° C., the active groups introduced into the polymer-based material may react with each other. Further, the polymer-based material may be deteriorated. Note that, a reaction time is properly set in accordance with the reaction temperature and the like. The reaction is brought about under the foregoing conditions, so that it is possible to easily introduce the active group into the polymer-based material.

A lower limit of an introduction ratio (% by weight) at which the active group is introduced into the polymer-based material is more preferably 0.1% by weight or more, still more preferably 1.0% by weight or more, particularly preferably 2.0% by weight or more. When the introduction ratio is less than 0.1% by weight, a smaller number of alkoxysilyl groups are introduced into the polymer-based material, so that it may be impossible to produce the titanium oxide complex. Meanwhile, an upper limit of the introduction ratio is more preferably 30% by weight or less, still more preferably 25% by weight or less, particularly preferably 20% by weight or less. When the introduction ratio exceeds 30% by weight, a larger number of the active groups are introduced into the polymer-based material, so that the active groups may react with each other.

Note that, the active group may be an active group contained in each polymer of the surface of the polymer-based material.

(Reactive Functional Group Introduction Step)

The following description explains a step of introducing a reactive functional group into the titanium oxide (reactive functional group introduction step). As a method for introducing the reactive functional group into the titanium oxide, specifically, a silane coupling agent having the reactive functional group is reacted with the titanium oxide for example.

Here, the silane coupling agent is described as follows. The silane coupling agent has a chemical structure represented by chemical formula (17).

$$Z-Si-(OR)_3 \qquad (17)$$

"Z" may be a reactive functional group which can chemically bond to an organic material such as various kinds of synthesis resin (the polymer-based material or the active group contained in the polymer-based material). Specifically, examples of the reactive functional group include groups, such as a vinyl group, an epoxy group, an amino group, a (meth)acryloxy group, and a mercapto group, which can form chemical bonds represented by the chemical formula (1) to the chemical formula (16). That is, the silane coupling agent used in the present embodiment has at least a reactive functional group. Further, "Si—(OR)$_3$" is a functional group which can chemically bond to the titanium oxide. Specifically, examples of "OR" include a methoxy group and an ethoxy group. Further, the reactive functional group Z in the chemical formula (17) and Si may bond to each other by a high molecular chain or a low molecular chain, or they may bond directly to each other. Further, the three "OR" may be identical to each other or different from each other. That is, at least one of the three "OR" is a functional group which can chemically bond to the titanium oxide.

That is, specifically, examples of the silane coupling agent include: a vinyl silane coupling agent such as vinyltrichlorosilane, vinyltrimethoxysilane, and vinyltriethoxysilane; an epoxy silane coupling agent such as β-(3,4 epoxycyclohexyl) ethyltrimethoxysilane, γ-glycydoxypropyltrimethoxysilane, γ-glycydoxypropylmethyldiethoxysilane, and γ-glycydoxypropyltriethoxysilane; a stilyl silane coupling agent such as p-stilyltrimethoxysilane; a methacryloxy silane coupling agent such as γ-methacryloxypropylmethyldimethoxysilane, γ-methacryloxypropyltrimethoxysilane, γ-methacryloxypropylmethyldiethoxysilane, and γ-methacryloxypropyltriethoxysilane; an acryloxy silane coupling agent such as γ-acryloxypropyltrimethoxysilane; an amino silane coupling agent such as N-β (aminoethyl) γ-aminopropyltrimethoxysilane, N-β (aminoethyl) γ-aminopropylmethyldimethoxymethoxysilane, N-β (aminoethyl) γ-aminopropyltriethoxysilane, γ-aminopropyltrimethoxysilane, γ-aminopropyltriethoxysilane, γ-triethoxy-N-(1,3-dimethylbutylidene) propylamine, N-phenyl-γ-aminopropyltrimethoxysilane, hydrochloride of N-(vinylbenzyl)-β-aminoethyl-γ-aminopropyltrimethoxysilane, and special aminosilane; a ureide silane coupling agent such as γ-ureidepropyltriethoxysilane; a chloropropyl silane coupling agent such as γ-chloropropyltrimethoxysilane; a mercapto silane coupling agent such as γ-mercaptopropyltrimethoxysilane and γ-mercaptopropylmethyldimethoxysilane; a sulfide silane coupling agent such as bis(triethoxypropyl)tetrasulfide; and an isocyanate silane coupling agent such as γ-isocyanatepropyltriethoxysilane. In the silane coupling agent mentioned above, it is preferable to use γ-methacryloxypropyltrimethoxysilane since it is a polymerizable monomer. The silane coupling agent is properly selected depending on a kind of the polymer-based material and a kind of the active group contained in the polymer-based material.

As described above, the silane coupling agent has the reactive functional group in its one end, and has the functional group in its other end, so that it is possible to favorably use the silane coupling agent. Note that, the reactive functional group can react with the active group. Further, the functional group can react with the titanium oxide. Further, the following description explains an example where the active group is introduced into the titanium oxide by using the silane coupling agent.

A reaction condition under which the silane coupling agent having the reactive functional group is reacted with the titanium oxide varies depending on a kind of reaction and a kind of the silane coupling agent used, and is not particularly limited. Further, as the kind of the reaction, for example, a dry method or a wet method is preferable.

In the case of the dry method, the titanium oxide particles are put into a high speed stirring apparatus, and the silane coupling agent having the functional group in its one end and the reactive functional group in its other end is dropped or sprayed so that the silane coupling agent is added to the titanium oxide particles. After evenly stirring the silane coupling agent and the titanium oxide particles, the resultant are dried. At this time, it is preferable that the amount of the added silane coupling agent is in a range of from 0.0001 to 10 weight parts with respect to 1 weight part of the titanium oxide particles.

Meanwhile, in the case of the wet method, the titanium oxide particles and the silane coupling agent are added to an organic solvent, and they are reacted with each other, while stirring them, within a temperature range from room temperature to 150° C., for 10 minutes to 10 days. Thereafter, the solvent and silane coupling agent that has not been reacted are removed, thereby drying the resultant.

At this time, examples of the used organic solvent include: a hydrocarbon solvent such as toluene and hexane; an ether solvent such as tetrahydrofuran and diethyl ether; a ketone solvent such as acetone and methylethylketone; and the like. A lower limit of the amount of the organic solvent used is more preferably 0.1 weight part or more, still more preferably 0.5 weight parts or more, with respect to 1 weight part of the titanium oxide (titanium oxide particles). When the amount of the organic solvent used is less than 0.1 weight part, it is difficult to uniform the reaction system, so that there is a case where the surface of the titanium oxide is not evenly modified. Meanwhile, an upper limit of the amount of the organic solvent used is more preferably 1000 weight parts or less, still more preferably 50 weight parts or less, with respect to 1 weight part of the titanium oxide particles. When the amount of the organic solvent used exceeds 1000 weight part, it is not economical.

A lower limit of the amount of the added silane coupling agent is more preferably 0.0001 weight part or more, still more preferably 0.001 weight part or more, with respect to 1 weight part of the titanium oxide particles. When the amount of the added silane coupling agent is less than 0.0001 weight part, an insufficient amount of the reactive functional group may be introduced into the surface of the titanium oxide particles. Meanwhile, an upper limit of the amount of the added silane coupling agent is more preferably 10 weight parts or less, still more preferably 5 weight parts or less, with respect to 1 weight part of the titanium oxide particles. When the amount of the added silane coupling agent exceeds 10 weight parts, it is not economical. Note that, this is true also in the case of the dry method.

Further, a lower limit of reaction temperature is more preferably not less than room temperature (25° C.). When the reaction temperature is less than the room temperature, it may take a long time to perform the reaction. Meanwhile, an upper limit of the reaction temperature is more preferably 150° C. or lower, still more preferably 100° C. or lower. When the reaction temperature exceeds 150° C., the reactive functional group and/or the functional group in an end of the silane coupling agent may bring about unfavorable side reaction.

Further, in order to keep photocatalyst activity of the titanium oxide into which the reactive functional group has been introduced in the reactive functional group introduction step, it is preferable that the reaction temperature is approximately 80° C.

(Reaction Step)

In the reaction step, (i) the active group introduced into the polymer-based material in the active group introduction step and (ii) the reactive functional group introduced into the titanium oxide in the reactive functional group introduction step are reacted with each other. Specifically, the polymer-based material is soaked in dispersion liquid in which the titanium oxide has been dispersed, so that the titanium oxide was adsorbed to the surface of the polymer-based material. Further, the reactive functional group and the active group are reacted with each other. Note that, the following description explains an example where the polymer-based material and the titanium oxide are bonded to each other on the basis of an amido bond by using silicone rubber as the polymer-based material.

Specifically, examples of dispersion medium in which the titanium oxide is dispersed include an organic solvent such as: water; a hydrocarbon solvent such as toluene and hexane; alcohols; an ether solvent such as tetrahydrofuran and diethyl ether; a ketone solvent such as acetone and methylethylketone; and the like. In the solvents mentioned above, it is preferable to use water and alcohols since the titanium oxide is favorably dispersed in them. Further, in case of using the hydrocarbon solvent such as toluene and hexane, it is possible to use, for example, (1) a method in which the titanium oxide is strongly stirred by means of a stirring apparatus such as a stirrer, (2) a method in which the titanium oxide is dispersed by means of an ultrasonic device, and (3) a method in which the stirring apparatus and the ultrasonic device are used together, in order to favorably disperse the titanium oxide.

In preparing the dispersion liquid, a lower limit of an amount of the added titanium oxide is more preferably 0.1% by weight or more, still more preferably 0.2% by weight or more, particularly preferably 0.5% by weight or more, with respect to the dispersion medium. When the amount of the added titanium oxide is less than 0.1% by weight, the titanium oxide is not evenly adsorbed to the surface of the polymer-based material, so that it may be impossible to form an even coating surface. Meanwhile, an upper limit of the amount of the added titanium oxide is more preferably 5.0% by weight or less, still more preferably 4.0% by weight or less, particularly preferably 3.0% by weight or less, with respect to the dispersion medium. When the amount of the added titanium oxide exceeds 5.0% by weight, the amount of the titanium oxide remaining in the dispersion solvent is much larger than the amount of the titanium oxide adsorbed to the surface of the polymer-based material, so that it is not economical.

A lower limit of reaction temperature at which the reactive functional group of the titanium oxide adsorbed to the surface of the polymer-based material and the active group are reacted with each other is more preferably 25° C. or higher, still more preferably 50° C. or higher, particularly preferably 80° C. or higher. When the reaction temperature is lower than 25° C., there is a case where the reactive functional group and the active group are not reacted with each other. Meanwhile, an upper limit of the reaction temperature is more preferably 200° C. or lower, still more preferably 175° C. or lower, particularly preferably 150° C. or lower. When the reaction temperature exceeds 200° C., the polymer-based material may be decomposed.

Note that, after soaking the polymer-based material into the dispersion liquid, it is preferable to wash the polymer-based material with the same solvent as the dispersion solvent before reacting them with each other. The titanium oxide is stacked on the surface of the polymer-based material having been soaked. Thus, when they are reacted with each other without being washed, they are made into a complex with the titanium oxide stacked, so that properties of the polymer-based material may be damaged, and its strength may be insufficient.

Further, the reaction may be performed under a vacuum condition as required. The reactive functional group of the titanium oxide and the active group of the polymer-based material are reacted with each other under a vacuum condition, so that it is possible to produce the titanium oxide complex more quickly. Note that, in case of performing the reaction under the vacuum condition, a pressure required in performing the reaction is preferably within a range of from 0.01 mmHg (1.33 Pa) to 10 mmHg (1.33 kPa).

Note that, the reaction condition in the reaction step, a kind of the solvent, and the like are properly changed depending on a kind of the polymer-based material, a kind of the reactive functional group and/or a kind of the active group.

(Titanium Oxide Complex)

The titanium oxide complex, according to the present embodiment, which is obtained in accordance with the foregoing production method, is arranged so that the titanium oxide chemically bonds to the surface of the polymer-based material. Specifically, the reactive functional group introduced into the titanium oxide and the active group contained in the polymer-based material chemically bond to each other. Thus, compared with a conventional titanium oxide complex, the titanium oxide is less likely to exfoliate from the polymer-based material. In other words, it is possible to fix the titanium oxide on the surface of the polymer-based material for an extended period of time. Thus, it is possible to provide the titanium oxide complex which can retain a function of the titanium oxide for an extended period of time.

Further, a thickness of a titanium oxide layer of thus obtained titanium oxide complex varies depending on a thickness of the polymer-based material and purpose of use thereof. For example, in case of using the titanium oxide complex in a percutaneous catheter, when the thickness of the polymer-based material is defined as 100%, the thickness of the titanium oxide layer is more preferably within a range of from 0.0001% to 100%, still more preferably within a range of from 0.001% to 10%. The thickness of the titanium oxide layer is set to be within the foregoing range, so that it is possible to obtain the titanium oxide complex superior in biocompatibility without damaging properties of the polymer-based material. Further, in the obtained titanium oxide complex, the titanium oxide bonds to the surface of the polymer-based material, so that the titanium oxide complex is superior in flexibility.

In this manner, the titanium oxide complex according to the present embodiment is superior in the flexibility, the strength, the adhesiveness with respect to an anatomy, and the biocompatibility, so that it is possible to favorably use the titanium oxide complex as a medical material such as: percutaneous medical apparatuses such as a percutaneous catheter and a percutaneous electric terminal; artificial organs such as an artificial blood vessel and prosthesis. Further, in the production method according to the present embodiment, it is possible to produce a titanium oxide complex having a more complicate shape with a simpler process than conventional ones.

Further, the titanium oxide is superior in disinfecting properties. Specifically, an ultraviolet ray is irradiated to ultraviolet ray photocatalyst titanium oxide or visible light is irradiated to visible light photocatalyst titanium oxide, so that it is possible to exhibit a disinfecting effect. Thus, in case where the titanium oxide complex according to the present embodiment is implanted in a living body as a percutaneous device (e.g., a catheter) for example, it is possible to kill various microorganism and the like, proliferating around a contact portion of the percutaneous device, which are harmful for a living body, and it is possible to easily prevent infection of the microorganism. Specifically, an ultraviolet ray is irradiated from the outside of the living body to the titanium oxide complex, so that it is possible to easily kill the bacteria. Thus, it is possible to prevent the infection. Thus, in case of producing a percutaneous device attached to an artificial organ and implanting the percutaneous device in the living body for an extended period of time for example, the titanium oxide complex according to the present embodiment is particularly favorably used as a medical polymer material required in (i) production of a material, implanted in a living body, which can suppress biological rejection and (ii) transfusion and production of a biological device used in furnishing of nutrition in home treatment.

Further, in order to control activity as the photocatalyst, it is possible to use titanium oxide particles coated with an organic substance or an inorganic substance in complexation. An example of the inorganic substance used in coating the surface includes hydroxy apatite, and an example of the organic substance includes a methacrylate compound, but the inorganic and organic substances are not limited to them.

Further, in the titanium oxide complex according to the present embodiment, it is possible to enables adsorption or desorption of cells in accordance with light, so that this is applicable to a petri dish used to prepare and incubate a cell sheet for regenerative medicine.

Further, the titanium oxide can be rooted (fixed) on the surface of the polymer-based material for an extended period of time, so that it is possible to favorably use the titanium oxide complex as a deodorant, an antibacterial and antimycotic material, a water-treatment material, an anticlouding material, and an antifoulant material.

Further, it is possible to provide a new method of modifying a surface of the polymer-based material with the titanium oxide.

Further, it is possible to stack, for example, a calcium phosphate compound on the titanium oxide complex according to the present embodiment as required. The calcium phosphate compound is superior in biological stability. Thus, it is possible to favorably use the calcium phosphate compound as a biomaterial by stacking the calcium phosphate compound on the titanium oxide complex according to the present embodiment.

Specific examples of a method of further stacking the calcium phosphate compound on the titanium oxide of the titanium oxide complex are as follows. (1) A method in which: particles obtained by mixing a polymerization monomer and the calcium phosphate compound are applied to the titanium oxide complex, i.e., to a surface obtained by modifying the polymer-based material with the titanium oxide, and the polymerization monomer is polymerized, so as to be solidified, by heat, light, radiation, or the like. (2) A method in which: the titanium oxide complex is soaked in a solution containing calcium ion and phosphate ion, so as to deposit the calcium phosphate compound. (3) A method in which: the titanium oxide complex is soaked in a solution containing calcium ion and a solution containing phosphate ion alternately, so as to deposit the calcium phosphate compound. Further, in case of the method (1), it is possible to stack the calcium phosphate compound in a desired shape by using a mold having an appropriate shape.

Embodiment 2

The following description explains other embodiment of the present invention. Note that, for convenience in description, the same reference signs are given to members having the same functions as members described in Embodiment 1, and description thereof is omitted.

A titanium oxide complex according to the present embodiment, in which titanium oxide chemically bonds to a polymer-based material having a functional group which is capable of chemically bonding to the titanium oxide, is arranged so that: the titanium oxide and the functional group chemically bond directly to each other.

A surface of the polymer-based material according to the present embodiment has the functional group which is capable of chemically bonding to the titanium oxide. "the titanium oxide and the functional group chemically bond directly to each other" means that the titanium oxide itself chemically bonds directly to the functional group. That is, in the titanium oxide complex of the present invention, the functional group contained in the polymer-based material and a hydroxyl group contained in the titanium oxide chemically bond to each other. A specific example of the functional group is at least one kind selected from a group of an alkoxysilyl group, an isocyanate group, and the like. The functional group on the surface of the polymer-based material may be a functional group contained in polymers of the surface of the base material, or may be a functional group introduced by reforming the surface of the polymer-based material in accordance with known means such as acid, or alkali treatment, corona discharge, plasma irradiation, surface graft polymerization, and the like.

Further, a method according to the present embodiment for producing the titanium oxide complex, in which titanium oxide chemically bonds to a polymer-based material, includes the steps of: introducing a functional group which is capable of chemically bonding to the titanium oxide; and reacting the functional group of the polymer-based material with the titanium oxide.

(Introduction Step)

In the introduction step, the functional group which is capable of chemically bonding to the titanium oxide is introduced into the polymer-based material. Note that, the following description explains a case where an alcoxysilyl group is introduced into the polymer-based material as a functional group which is capable of chemically bonding to the titanium oxide.

The method for introducing the functional group into the polymer-based material, i.e., the introduction step is performed by a known method, and is not particularly limited. However, by using a silane coupling agent or the like having a functional group on its end, it is possible to introduce the functional group into the polymer-based material.

Here, as a method for introducing the alcoxysilyl group into the polymer-based material, an introduction method using the silane coupling agent is described as follows. Note that, the method for introducing the alcoxysilyl group into the polymer-based material is not limited to this method, and it is possible to adopt various methods.

A specific example of the introduction method using the silane coupling agent is as follows. The silane coupling agent having the functional group in its end is directly introduced into the polymer-based material having been subjected to the corona treatment. Further, proton (hydrogen atom) is drawn from the polymer-based material by using an surface-active agent and a peroxyde initiator so as to bring about a free radical, thereby performing graft polymerization so that a water-insoluble monomer having the functional group is polymerized directly with the polymer-based material. By adopting this method, it is possible to introduce the functional group directly, which is capable of chemically bonding to the titanium oxide, into the polymer-based material.

Further, as the method for introducing the alcoxysilyl group into the polymer-based material, for example, it may be so arranged that: an active group which can react with a reactive functional group contained in the silane coupling agent is introduced into the polymer-based material in advance, and the active group and the reactive functional group of the silane coupling agent are reacted with each other, thereby introducing the alcoxysilyl group into the polymer-based material. Note that, specific examples of the active group include a vinyl group and an amino group, but the active group is not particularly limited. The active group is properly set depending on a kind of the reactive functional group ("Z" in the chemical formula (17)) of the silane coupling agent. Thus, the silane coupling agent used in the present embodiment has at least the functional group, and it is more preferable that the silane coupling agent used in the present embodiment has the functional group and the reactive functional group. Note that, the functional group can chemically bond to the titanium oxide itself (hydroxyl group contained in the titanium oxide), and the reactive functional group can chemically bond to the active group or the polymer-based material itself.

Here, silkfibroin is used as the polymer-based material, and a vinyl group which functions as the active group is introduced into silkfibroin, and the vinyl group and the reactive functional group of the silane coupling agent are reacted with each other, thereby introducing the alcoxysilyl group (Si—OR) into the polymer-based material. The following description explains a specific example thereof.

The step of introducing the active group into the polymer-based material is the same as the active group introduction step of Embodiment 1, so that detailed description thereof is omitted.

Next, the active group introduced into the polymer-based material and the silane coupling agent having the reactive functional group and the functional group in its ends are polymerized with each other, thereby introducing the alcoxysilyl group, which functions as the functional group, into the polymer-based material.

Any silane coupling agent may be used as long as the silane coupling agent has the functional group and the reactive functional group contained in the end can be polymerized with the active group introduced into the polymer-based material. Thus, the silane coupling agent is not particularly limited. However, in case where the vinyl group is introduced as the active group, it is possible to favorably use a methacryloxy silane coupling agent such as γ-methacryloxypropyltrimethoxysilane.

Further, the silane coupling agent and the polymer-based material in which the active group has been introduced are polymerized with each other in the presence of a polymerization initiator and a solvent, it is possible to introduce the alcoxysilyl group, which functions as the functional group, into the polymer-based material.

As the solvent, it is preferable to use a nonpolar organic solvent such as a hydrocarbon solvent, e.g., toluene, hexane, and the like.

Further, as the polymerization initiator, it is preferable to use azobisisobutyronitrile, benzoyl peroxide, and the like, for example.

A lower limit of the amount of the silane coupling agent used (added) is more preferably 10% by weight or more, still more preferably 50% by weight or more, particularly preferably 100% by weight, with respect to the polymer-based material in which the active group has been introduced. When the amount of the silane coupling agent used is less than 10% by weight, it may be impossible to introduce so sufficient alcoxysilyl group that the alcoxysilyl group can react with the titanium oxide. Meanwhile, an upper limit of the amount used is more preferably 500% by weight or less, still more preferably 400% by weight or less, particularly preferably 300% by weight or less. When the amount used exceeds 500% by weight, it is not economical.

Further, it is more preferable to perform the polymerization under an atmosphere of nitrogen. A lower limit of the polymerization temperature is more preferably 40° C. or higher, still more preferably 45° C. or higher, particularly preferably 50° C. or higher. When the polymerization temperature is lower than 40° C., the polymerization insufficiently occurs, so that there is a case where the functional group is not introduced into the polymer-based material. Meanwhile, an upper limit of the polymerization temperature is more preferably 80° C. or lower, still more preferably 75° C. or lower, particularly preferably 70° C. or lower. When the polymerization temperature exceeds 80° C., the polymer-based material may be deteriorated. Note that, a polymerization time is properly set so as to realize a desired introduction ratio (a ratio at which the functional group is introduced into the polymer-based material).

Further, a lower limit of the introduction ratio (% by weight) of the functional group with respect to the polymer-based material is more preferably 0.1% by weight or more, still more preferably 1% by weight or more. Here, the introduction ratio is a ratio of a weight of the silane coupling agent introduced into the polymer-based material for each unit weight. When the introduction ratio exceeds 0.1% by weight, it is possible to bond the titanium oxide, whose amount is so sufficient that it is possible to exhibit biocompatibility, to the polymer-based material. Meanwhile, an upper limit of the introduction ratio is not particularly limited. However, when the introduction ratio exceeds 100% by weight, the amount of the titanium oxide bonded to the polymer-based material is too large, so that it is not economical.

Note that, a method for introducing the alcoxysilyl group into the polymer-based material is not limited to the method described above, but it is possible to adopt various methods. Further, the reaction condition is properly set depending on kinds of the polymer-based material, the compound having the active group, and the silane coupling agent, and the like, and the reaction condition is not particularly limited. In this manner, it is possible to introduce the functional group into the surface of the polymer-based material.

Note that, in case where the functional group is an isocyanate group and the isocyanate group is introduced into the polymer-based material by polymerizing a monomer having the isocyanate group in its end with the polymer-based material, the isocyanate group reacts with active hydrogen in the reaction solvent, so that the isocyanate group may be deactivated. Thus, it is preferable to react them with each other in an anhydrous solvent such as anhydrous dimethylsulfoxide and anhydrous dimethylformamido.

Further, in case of reacting (polymerizing) a monomer having an isocyanate group in its end with the polymer-based material in water or alcohol having active hydrogen, it is necessary to protect the isocyanate group since the isocyanate group reacts with the active hydrogen. Specifically, by using a block agent such as phenol, imidazole, oxime, N-hydroxyimide, alcohol, lactam, and an active methylene complex so as to protect the isocyanate group, it is possible to perform the polymerization. It is possible to remove the block agent which protects the isocyanate group by heating the block agent in advance. Thus, the isocyanate group is protected by the block agent, and the monomer contained in the other end and the polymer-based material are polymerized, and they are heated, so that it is possible to introduce the isocyanate group into the polymer-based material. That is, it is possible to obtain the polymer-based material having the isocyanate group in its surface.

For example, in case of using phenol as the block agent, the block agent is heated within a range of from 110 to 120° C., so that it is possible to remove the block agent which protects the isocyanate group. For example, in case of using imidazole as the block agent, the block agent is heated within a range of from 110 to 130° C., so that it is possible to remove the block agent which protects the isocyanate group. In case of using oxime as the block agent, the block agent is heated within a range of from 130 to 150° C., so that it is possible to remove the block agent which protects the isocyanate group. Specific examples of the block agent include: a phenol-containing compound such as methylsalicylate and methyl-p-hydroxybenzoate; imidazole; and an oxime-containing compound such as methylethylketoxime and acetoneoxime. Further, it is possible to use, for example, an N-hydroxyimido-containing compound such as N-hydroxyphthalimide and N-hydroxysuccinimide; an alcohol-containing compound such as methoxypropanol, ethylhexanol, pentol, and ethyllactate; a lactam-containing compound such as caprolactam and pyrolidinon; and an active methylene compound such as ethylacetoacetate, depending on a kind of the polymer-based material.

Note that, as to the case of using isocyanate as the functional group, other reaction conditions (for example, an amount of isocyanate added to the polymer-based material) are set in the same manner as in the case of using the alcoxysilyl group as the functional group, and detailed description thereof is omitted.

(Functional Group Reaction Step)

In the functional group reaction step, the functional group (for example, the isocyanate group or the alcoxysilyl group) introduced into the polymer-based material and the titanium oxide are reacted with each other. The functional group reaction step is performed under the same condition as the aforementioned reaction step, so that detailed description thereof is omitted.

(Titanium Oxide Complex)

The titanium oxide complex according to the present embodiment, in which titanium oxide chemically bonds to a polymer-based material having a functional group which is capable of chemically bonding to the titanium oxide, is arranged so that the titanium oxide chemically bonds to the functional group contained in the polymer-based material.

It is possible to produce the titanium oxide obtained in the foregoing manner without further modifying a surface of the titanium oxide (it is not necessary to perform pretreatment).

Further, a method according to the present embodiment for producing the titanium oxide complex, in which titanium oxide chemically bonds to a polymer-based material having a functional group which is capable of chemically bonding to the titanium oxide, includes: an introduction step of introducing the functional group, which is capable of chemically bonding to the titanium oxide, into the polymer-based material; and a reaction step of reacting the functional group of the polymer-based material with the titanium oxide.

Further, it is more preferable that the titanium oxide complex according to the present embodiment is produced by the foregoing production method of the titanium oxide complex.

Further, it is preferable that: the method according to the present embodiment for producing the titanium oxide complex further includes an active group introduction step of introducing an active group into the polymer-based material before performing the introduction step, wherein a compound having a reactive functional group and a functional group which is capable of chemically bonding to the titanium oxide is used to react the reactive functional group and the active group with each other.

According to the arrangement, the active group which can react with the reactive functional group can be introduced into the polymer-based material, so that it is possible to select many kinds of the reactive functional group. Thus, it is possible to introduce the functional group more easily.

Further, it may be so arranged that: the method according to the present invention for producing the titanium oxide complex, in which titanium oxide chemically bonds to a polymer-based material, includes a reaction step of chemically bonding the titanium oxide with the polymer-based material.

According to the arrangement, the titanium oxide and the polymer-based material chemically bond to each other, so that it is possible to provide the titanium oxide complex in which the titanium oxide and the polymer-based material firmly bond to each other compared with conventional ones.

Further, it may be so arranged that: the method according to the present invention for producing the titanium oxide complex, in which titanium oxide chemically bonds to a polymer-based material, includes: a reactive group introduction step of introducing a reactive group, which is capable of reacting with the polymer-based material, into the titanium oxide; and a bonding step of reacting the reactive group with the polymer-based material.

Further, at this time, a silane coupling agent having the reactive group in its one end and the reactive functional group in its other end is used, so that it is possible to produce the titanium oxide complex more easily.

EXAMPLE

The following Example and Comparative Example further detail the present invention, but the present invention is not limited to them at all.

The following description explains Example of a case where: the active group is introduced into the polymer-based material, and the reactive functional group which can react with the active group is introduced into the titanium oxide, and the active group and the reactive functional group are reacted with each other, thereby producing the titanium oxide complex.

(Titanium Oxide)

Titanium oxide particles (particle diameter is 200 to 300 nm, anatase-type, specific surface area is 5 m$^2$/g: product of ISHIHARA SANGYO KAISHA, CO., LTD.) was dried at 120° C. for 24 hours. Thereafter, 5.0 g of the titanium oxide particles, 150 ml of toluene anhydride, and 5.0 ml of γ-aminopropyltriethylsilane (product of Shin-Etsu Chemical Co., Ltd., product number: KBE903) were placed in a three-neck flask whose volume was 300 ml, and were refluxed for 6 hours, thereby obtaining aminated titanium oxide in which an amino group had been introduced into the titanium oxide. Note that, in order to confirm whether the amino group had been introduced or not, infrared spectra of (a) γ-aminopropyltriethylsilane, (b) untreated anatase-type titanium oxide particles, (c) titanium oxide particles in which the amino group had been introduced (reacted for 30 minutes), and (d) titanium oxide particles in which the amino group had been introduced (reacted for 6 hours) were measured. FIG. 1 shows the result of the measurement. The result of FIG. 1 shows that the amino group was introduced into the titanium oxide.

Further, thus obtained aminated titanium oxide was purified with a large amount of toluene in accordance with centrifugation, and was dried at 60° C. for the whole day and night.

(Silicone Rubber)

Meanwhile, a surface of a silicone rubber sheet, used as the polymer-based material, whose thickness was 0.3 mm, was treated by corona discharge. Further, the silicone rubber and 25 ml of 10% by weight acrylic aqueous solution were placed in a polymerization tube, and were deaerate under a reduced pressure. Thereafter, they were polymerized with each other at 60° C. for an hour while being sealed, thereby performing graft polymerization so that acrylic acid was polymerized with a surface of the silicone rubber. Thus, a silicone rubber sheet (carboxyl-group-introduced silicone sheet) in which a carboxyl group had been introduced into the surface of the silicone rubber was obtained.

(Titanium Oxide Complex)

Figure 2:
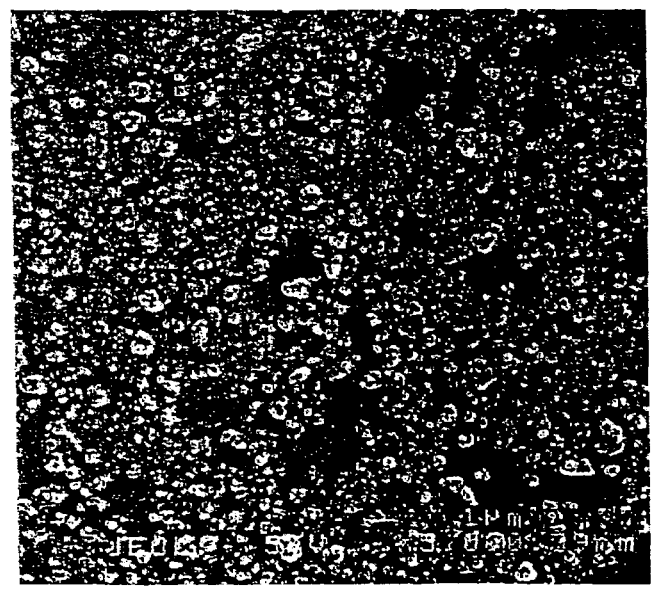
FIG. 2 shows an image obtained by observing a surface of a titanium oxide complex of Example through an electron microscope.

Further, 40 mg of aminated titanium oxide particles in which the amino group had been introduced was sufficiently dispersed in 20 ml of distilled water so as to prepare dispersion liquid. Thereafter, the carboxyl-group-introduced silicone sheet having been cut in a round shape of 1.5 cm was soaked and left at rest in the dispersion liquid for an hour, thereby causing the titanium oxide particles to be adsorbed to the surface of the silicone sheet. Thereafter, the silicone rubber sheet having the titanium oxide particles was picked up, and the silicone rubber sheet was washed with flowing water for a long time. Next, the washed silicone rubber sheet was heated at 180° C., under a reduced pressure of 1 mmHg, for 6 hours so that an amido bond was formed, thereby obtaining the titanium oxide complex. Thus obtained titanium oxide complex was observed by a scanning electron microscope (hereinafter, referred to as SEM). As shown in FIG. 2, an image obtained in the foregoing observation shows that the titanium oxide chemically bonds to the surface of the silicone rubber sheet.

(Cell Adhesion Test)

Figure 3:
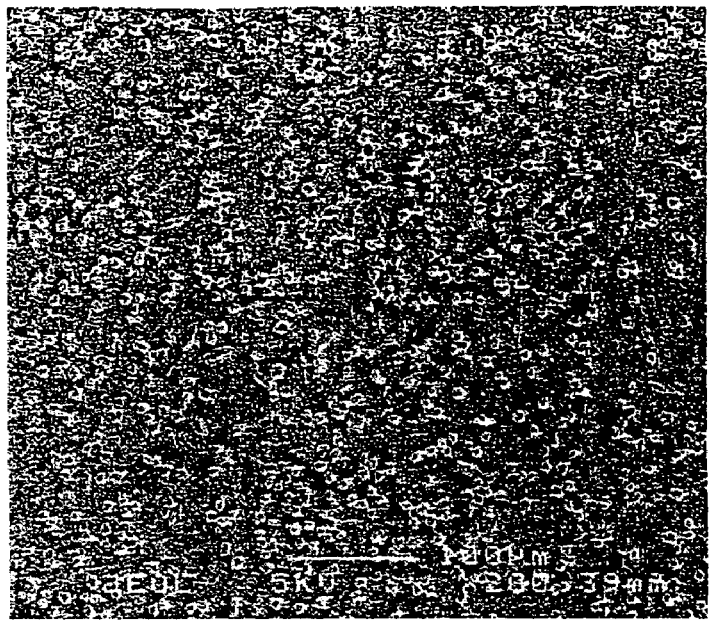
FIG. 3 shows an image obtained by observing the surface of the titanium oxide complex through the electron microscope when cells are fixed by using the titanium oxide complex of Example.

The titanium oxide complex sheet (diameter was 1.5 cm) of the Example was placed on a 24 multiwell, and 1×10$^5$ mouse fibroblasts (L929 cells) were seeded, and were incubated for 24 hours. Thereafter, the sheet was picked up, and was washed with phosphate buffer three times. Thus washed sheet was fixed with 10% neutral buffered formalin, and was dehydrated with ethanol and the like. Thereafter, ethanol was replaced with butanol, thereby performing freeze dry. Further, the sheet that had been subjected to the freeze dry was coated with platinum, and a condition under which cells adhered to the titanium oxide complex was observed as a SEM sample by means of the SEM. FIG. 3 shows the result of the observation. The result shows that cells favorably adhere to the surface of the titanium oxide complex.

COMPARATIVE EXAMPLE

Figure 4:
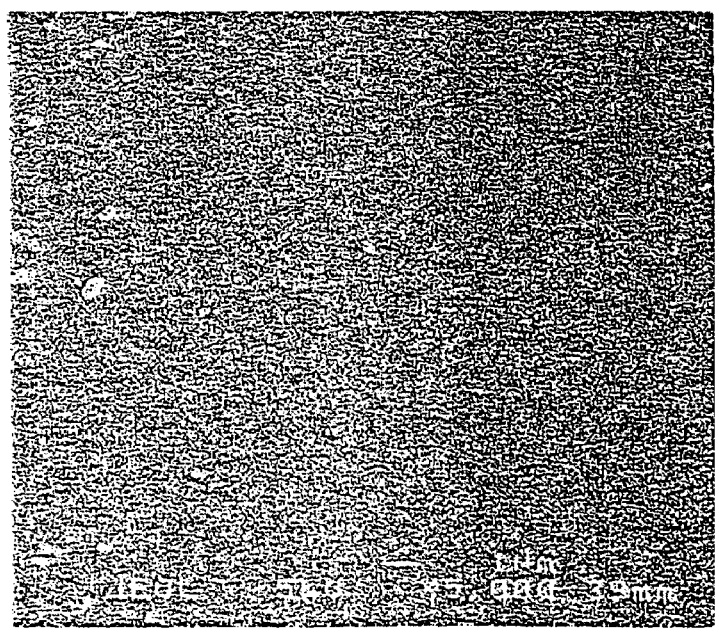
FIG. 4 shows an image obtained by observing a surface of a titanium oxide complex of Comparative Example through the electron microscope

The same steps as in the Example were performed except that an untreated silicone rubber sheet in which the carboxylic group had not been introduced was soaked in the dispersion liquid of untreated anatase-type titanium oxide in which the amino group had not been introduced, thereby obtaining a titanium oxide complex. Thus obtained titanium oxide complex was observed by means of the SEM. FIG. 4 shows the result of the observation.

Figure 5:
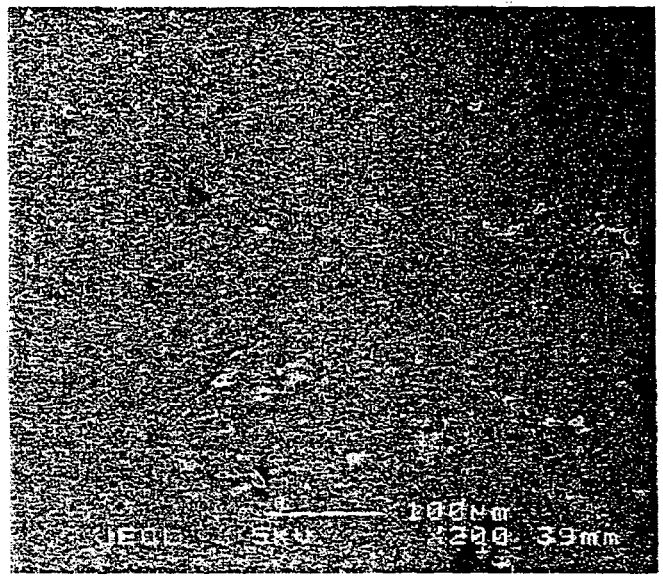
FIG. 5 shows an image obtained by observing the surface of the titanium oxide complex through the electron microscope when cells are fixed by using the titanium oxide complex of Comparative Example.

Further, the cell adhesion test was performed as in the Example. FIG. 5 shows the result of the cell adhesion test. The result shows that no adhesion of cells was found in case where the untreated silicone rubber sheet was used.

(Photocatalyst Activity of Aminated Titanium Oxide)

As to the aminated titanium oxide, measurement was performed with respect to (i) photocatalyst activity of the aminated titanium oxide produced by varying a reaction time and (ii) photocatalyst activity of the aminated titanium oxide produced in the same manner except that reflux had been performed at reaction temperature of 80° C.

Specifically, 70 mg of the aminated titanium oxide particles produced by varying the reaction temperature and 70 mg of the aminated titanium oxide particles produced by varying the reaction time were respectively placed into sealing glass vessels. Further, each of the glass vessels was filled with acetaldehyde so that concentration thereof was 300 ppm. Light of a xenon lamp (2000 μW) was exposed to the glass vessel. After a predetermined time had passed, 0.5 ml of gas was sampled from the glass vessel, and the acetaldehyde concentration in the gas was measured in accordance with gas chromatography. On the basis of the result (variation of the acetaldehyde concentration), an acetaldehyde decomposition rate coefficient was calculated. The results are shown in Tables 1 and 2 (Table 1 shows the result of the aminated titanium oxide (samples 1 to 6), produced by varying a reaction time at which the amino group had been introduced, while performing reaction at reaction temperature of 120° C., and Table 2 shows the result of the aminated titanium oxide (samples 7 to 9), produced by varying a reaction time at which the amino group had been introduced, while performing reaction at reaction temperature of 80° C.). It is found that: as the acetaldehyde decomposition rate coefficient is larger, the photocatalyst activity is higher. Note that, in Tables 1 and 2, the acetaldehyde decomposition rate coefficient corresponding to the reaction time of 0 minute indicates a value in case of using the titanium oxide that has not been aminated.

TABLE 1

| | Reaction Temperature (° C.) | Reaction Time (Minutes) | Acetaldehyde Decomposition Rate Coefficient |
|---|---|---|---|
| SAMPLE 1 | 120 | 0 | 31.2 |
| SAMPLE 2 | 120 | 10 | 1.03 |
| SAMPLE 3 | | 30 | 0.61 |
| SAMPLE 4 | | 90 | 0.29 |
| SAMPLE 5 | | 120 | 0.24 |
| SAMPLE 6 | | 180 | 0.30 |

TABLE 2

| | Reaction Temperature (° C.) | Reaction Time (Minutes) | Acetaldehyde Decomposition Rate Coefficient |
|---|---|---|---|
| SAMPLE 7 | 80 | 0 | 31.2 |
| SAMPLE 8 | 80 | 10 | 23.3 |
| SAMPLE 9 | | 30 | 5.8 |

The result shows that also the aminated titanium oxide has the photocatalyst activity. That is, it is found that the titanium oxide complex produced by using the aminated titanium oxide has the photocatalyst activity. Further, the result shows that the titanium oxide complex has antimicrobial properties. Further, it is found that: the aminated titanium oxide produced at reaction temperature of 80° C. has higher photocatalyst activity even when it takes less reaction time to aminate the titanium oxide.

(Antimicrobial Property Test of Titanium Oxide Complex)

Preparation of bacterial liquid for photocatalyst antibacterial effect test

An *Escherichia coli* (NBRC3301) for antimicrobial effect test was awaken from a state of preservation so as to be in an active state. Further, 5 ml (5,000 µl) of sterile physiological saline solution (0.09 mol/L) was placed in a centrifugation tube. Thereafter, 0.5 ml (500 µl) bacterial liquid of the *Escherichia coli* was sampled, thus sampled *Escherichia coli* was placed in the centrifugation tube, and was stirred. Further, centrifugal separation was performed at 1,000 rpm for 5 minutes, and supernatant liquid thereof was excluded, and a culture medium component was removed. Next, 5 ml of sterile physiological saline was added to the remaining precipitate, thereby suspending the precipitate. Further, absorbance of the bacterial liquid at a wavelength of 600 nm was measured, and the bacterial liquid was diluted so that the bacterial concentration was $10^5$/ml in accordance with the absorbance, thereby preparing the bacterial liquid for photocatalyst antimicrobial effect test of the titanium oxide complex (titanium oxide-silicone coat) (hereinafter, referred to as *Escherichia coli* liquid).

Antibacterial Effect Test

A sample (titanium oxide complex: titanium oxide-silicone coat (Φ15 mm)) was placed on a petri dish under an sterile condition, and the sample was fixed by a ring so as to suppress the sample from floating when the *Escherichia coli* liquid was poured therein.

Next, 500 (µl) of the *Escherichia coli* liquid ($10^5$/ml) prepared by setting the bacterial amount was evenly dropped to a surface of the sample.

Figure 6:
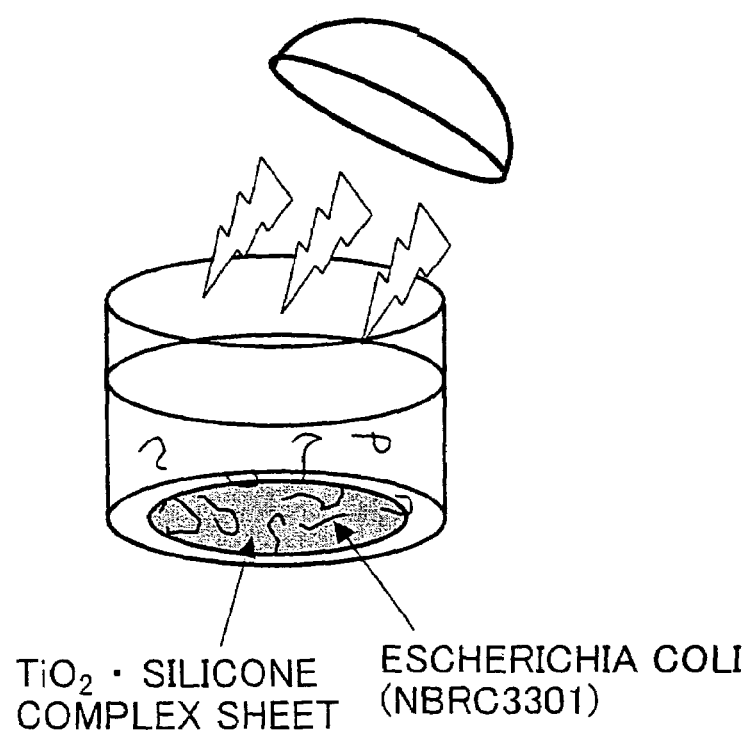
FIG. 6 is a front view schematically showing an apparatus for carrying out an antibacterial property test.

Further, as shown in FIG. 6, the petri dish on which the bacteria had been placed was placed on a sample table in an ultraviolet irradiation room, and an ultraviolet light (wavelength was 350 nm) was irradiated for a certain time at temperature of 25° C. and at humidity of 70%.

More specifically, a black light (product of TOPCON CORPORATION, type FI-5L) was used to irradiate an ultraviolet light (irradiation wavelength ranged from approximately 300 to 400 nm, peak wavelength was approximately 350 nm) to the sample for 120 minutes.

Further, after irradiating the ultraviolet light for 120 minutes, the sample was picked up, and the sample was diluted to 1/5 with sterile physiological saline solution. Further, 100 µl of thus diluted sample was divided and placed on three sheets of agar medium by using a pipette.

Figure 7:
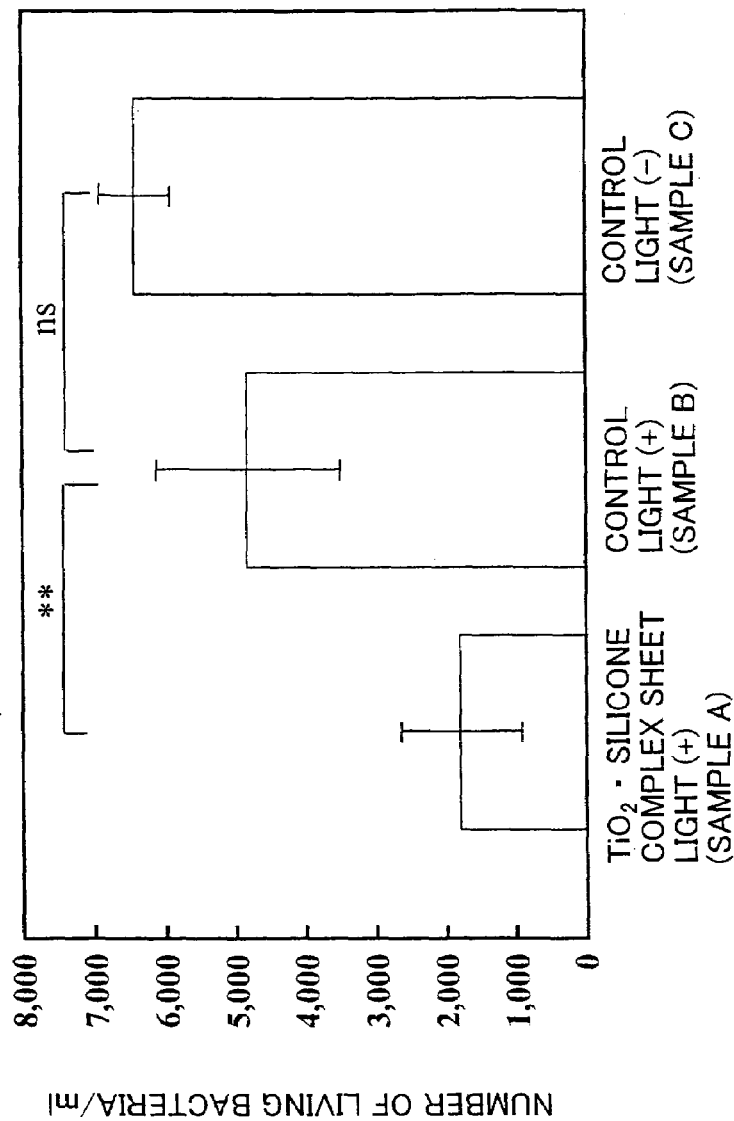
FIG. 7 is a graph showing a result obtained by carrying out the antibacterial property test.

Thereafter, the agar mediums containing thus divided samples were incubated by a light-shielding incubator at 37° C. for 16 hours. Further, the petri dish was pulled out, and colonies of the *Escherichia coli* were marked at a rear face of the petri dish by using a pen, and the marked colonies were counted, thereby counting the number of living bacteria. Further, the foregoing test was repeated four times (sample A). Table 3 and FIG. 7 show (i) the number of *Escherichia coli* remaining after irradiating the ultraviolet light for 120 minutes and (ii) its standard deviation (n=4) that were calculated from the number of living bacteria on the agar mediums.

COMPARATIVE EXAMPLE

The same operation as in the antimicrobial effect test was performed except that mere the *Escherichia coli* liquid was poured without placing the titanium oxide complex in the petri dish (sample B). Table 3 and FIG. 7 show the result.

Further, the same operation as in the antibacterial effect test was performed except that mere the *Escherichia coli* liquid was poured and left in a dark place for 120 minutes without placing the titanium oxide complex in the petri dish and without irradiating the ultraviolet light (sample C). Table 3 and FIG. 7 show the result.

Note that, in the following result, the sample to which the ultraviolet light was irradiated is referred to as the sample A (Example), and the sample containing mere the *Escherichia coli* is referred to as the sample B (Comparative Example), and the sample, containing mere the *Escherichia coli*, to which the ultraviolet light was not irradiated, is referred to as the sample C (Comparative Example).

TABLE 3

| | Average Number of *Escherichia Coli* | Standard Deviation |
|---|---|---|
| SAMPLE A | 1775 | 1733 |
| SAMPLE B | 4819 | 2610 |
| SAMPLE C | 6413 | 974 |

In accordance with a statistical treatment performed with respect to the result of Table 3 and FIG. 7 by using t-test, a statistical difference was found between the samples A and B, and a statistical difference was found between the samples A and C. Further, no statistical difference was found between the samples B and C. Thus, these results show that the titanium oxide complex of the present invention has antimicrobial properties.

The foregoing results show that: in the titanium oxide complex of the present Example, the titanium oxide bonds to the polymer-based material. Further, also in the cell adhesion test, it is found that the titanium oxide complex of the present Example favorably adheres to the cells. Thus, it is found that the titanium oxide complex of the present Example can be favorably used as a medical material.

As described above, the titanium oxide complex of the present invention includes: a polymer-based material having an active group; and titanium oxide having a reactive functional group which is capable of reacting with the active group, wherein the active group and the reactive functional group are bonded to each other based on a chemical bond.

According to the arrangement, the titanium oxide and the polymer-based material chemically bond to each other. Thus, compared with a conventional titanium oxide complex, it is possible to firmly fix the titanium oxide and the polymer-based material to each other. Therefore, it is possible to fix (root) the titanium oxide to a surface of the polymer-based material for an extended period of time.

Further, according to the arrangement, a combination which enables the active group and the reactive functional group to enter into a chemical bond is selected, so that it is possible to chemically bond the polymer-based material and the titanium oxide to each other more easily.

As described above, the titanium oxide complex of the present invention, obtained by chemically bonding titanium oxide to a polymer-based material having a functional group which is capable of chemically bonding to the titanium oxide, is arranged so that the titanium oxide and the functional group chemically bond directly to each other.

"The titanium oxide and the functional group, which is capable of reacting with the titanium oxide of the polymer-based material, chemically bond directly to each other" means that the titanium oxide and the functional group chemically bond directly to each other. That is, in the titanium oxide complex of the present invention, the polymer-based material and the titanium oxide itself chemically bond to each other.

Examples of a complexation method of the titanium oxide are as follows. (1) A method in which: after modifying a surface of the titanium oxide and/or the polymer-based material (surface treatment), both the titanium oxide and the polymer-based material are made to chemically bond to each other. (2) A method in which: the titanium oxide and the polymer-based material are made to chemically bond to each other without performing the surface treatment.

As to the method (1), it is not necessary to perform chemical pretreatment with respect to the titanium oxide in a process of performing the surface treatment with respect to merely the polymer-based material, that is, a process of chemically bonding (i) the titanium oxide which has not been subjected to any chemical surface treatment directly to (ii) the functional group which is capable of chemically bonding to the titanium oxide of the polymer-based material. Note that, the chemical surface treatment means to introduce the active group and the like into the titanium oxide.

Further, the titanium oxide itself and the functional group of the polymer-based material are made to chemically bond directly to each other, so that there is no possibility that the active group remaining on the surface of the titanium oxide may damage a characteristic (property) of the titanium oxide compared with the arrangement in which the active group is introduced into the titanium oxide.

As described above, the medical material of the present invention includes the foregoing titanium oxide complex.

According to the arrangement, the medical material is arranged by using the foregoing titanium oxide complex. Thus, even in case of implanting the titanium oxide complex in a living body for an extended period of time, it is possible to provide a medical material having higher reliability.

As described above, a method of the present invention for producing a titanium oxide complex, obtained by chemically bonding titanium oxide to a polymer-based material having a functional group which is capable of chemically bonding to the titanium oxide, includes: an active group introduction step of introducing an active group into a polymer-based material; a reactive functional group introduction step of introducing a reactive functional group, which is capable of reacting with the active group, into titanium oxide; and a reaction step of reacting the active group with the reactive functional group.

According to the arrangement, the active group is introduced into the polymer-based material, and the reactive functional group is introduced into the titanium oxide, thereby chemically bonding the active group and the reactive functional group to each other. Thus, it is possible to easily produce the titanium oxide complex in which the titanium oxide and the polymer-based material chemically bond to each other.

It is more preferable to arrange the method of the present invention for producing the titanium oxide complex so that a silane coupling agent having the reactive functional group is used in the reactive functional group introduction step.

By using the silane coupling agent, it is possible to more easily introduce the reactive functional group into the titanium oxide.

As described above, a method of the present invention for producing a titanium oxide complex, obtained by chemically bonding titanium oxide to a polymer-based material having a functional group which is capable of chemically bonding to the titanium oxide, includes an introduction step of introducing a functional group, which is capable of chemically bonding to a hydroxyl group contained in titanium oxide, into the polymer-based material; and a functional group reaction step of reacting the functional group of the polymer-based material with the hydroxyl group contained in the titanium oxide.

According to the arrangement, the functional group which is capable of chemically bonding to the titanium oxide is introduced into the polymer-based material, so that it is not necessary to perform chemical pretreatment with respect to the titanium oxide. Thus, there is no possibility that the chemical pretreatment may damage or denature a property of the titanium oxide.

It is more preferable to arrange the method of the present invention for producing the titanium oxide complex so that the functional group is at least one kind selected from a group of an alcoxysilyl group and an isocyanate group.

The alcoxysilyl group and the isocyanate group are capable of chemically bonding directly to the titanium oxide, so that they are favorably used.

It is more preferable to arrange the method of the present invention for producing the titanium oxide complex so that a silane coupling agent having the functional group is used in the introduction step.

By using the foregoing silane coupling agent, it is possible to more easily introduce the functional group into the titanium oxide.

Further, it is more preferable to arrange the method of the present invention for producing the titanium oxide complex so that the polymer-based material is a medical polymer material.

According to the arrangement, the polymer-based material is the medical polymer material, so that it is possible to produce the titanium oxide complex having high biocompatibility.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The titanium oxide complex of the present invention can be favorably used as a medical material such as a percutaneous catheter, and as a photocatalyst, a deodorant, an antifoulant, an antibacterial/antiviral/antifungal agent, an anticlouding agent, a water-treatment agent, an anticancer agent (material), and the like.

The invention claimed is:

1. A polymer-based material chemically bonded to titanium oxide, comprising:
   the polymer-based material having an active group; and the titanium oxide having an amino group which is capable of reacting with the active group, wherein the active group and the amino group are bonded directly to each other based on an amido bond and wherein said titanium oxide is chemically bonded to said polymer-based material.

2. The polymer-based material chemically bonded to titanium oxide as set forth in claim 1, wherein the polymer-based material is silicone rubber.

3. The polymer-based material chemically bonded to titanium oxide as set forth in claim 1, wherein the titanium oxide having the reactive functional group which is capable of reacting with the active group has a photocatalyst property.

4. A medical material, comprising the polymer-based material chemically bonded to titanium oxide as set forth in claim 1.

5. A method of producing a titanium oxide bonded to a polymer based material, comprising:
   an active group introduction step of introducing an active group into the polymer-based material as in claim 1;
   a reactive functional group introduction step of introducing a reactive functional group, which is capable of reacting with the active group, into the titanium oxide; and
   a reaction step of reacting the active group with the reactive functional group.

6. The method as set forth in claim 5, wherein a silane coupling agent having the reactive functional group is used in the reactive functional group introduction step.

7. The method as set forth in claim 5, wherein the active group is a carboxyl group, and the reactive functional group is an amino group.

8. The method as set forth in claim 5, wherein the polymer-based material is a medical polymer material.

9. A titanium oxide bonded to a polymer based material, comprising: a hydroxyl group contained in the titanium oxide; and the polymer-based material having an alkoxysilyl group which is capable of chemically bonding to the hydroxyl group, wherein the hydroxyl group and the polymer-based material are bonded directly to each other based on a chemical bond and wherein said titanium oxide is chemically bonded to said polymer-based material.

10. The titanium oxide bonded to a polymer based material as set forth in claim 9, wherein the polymer-based material is silkfibroin.

11. A medical material, comprising the titanium oxide bonded to a polymer based material as set forth in claim 9.

12. A method of producing a titanium oxide bonded to a polymer-based material as in claim 6, comprising:
    an introduction step of introducing a functional group, which is capable of chemically bonding to a hydroxyl group contained in the titanium oxide, into the polymer-based material; and
    a functional group reaction step of reacting the functional group of the polymer-based material with the hydroxyl group contained in the titanium oxide.

13. The method as set forth in claim 12, wherein the functional group is at least one kind selected from a group of an alcoxysilyl group and an isocyanate group.

14. The method as set forth in claim 12, wherein a silane coupling agent having the functional group is used in the introduction step.

15. The method as set forth in claim 12, wherein the polymer-based material is a medical polymer material.

* * * * *